US010533949B2

(12) United States Patent
Charlton

(10) Patent No.: US 10,533,949 B2
(45) Date of Patent: Jan. 14, 2020

(54) TEST STRIP METER WITH A MECHANISM FOR PUSHING THE TEST STRIP AGAINST AN OPTICAL READER

(71) Applicant: BAYER HEALTHCARE LLC, Whippany, NJ (US)

(72) Inventor: Steven C. Charlton, Osceola, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 467 days.

(21) Appl. No.: 14/774,114

(22) PCT Filed: Mar. 7, 2014

(86) PCT No.: PCT/US2014/021691
§ 371 (c)(1),
(2) Date: Sep. 9, 2015

(87) PCT Pub. No.: WO2014/164279
PCT Pub. Date: Oct. 9, 2014

(65) Prior Publication Data
US 2016/0025638 A1 Jan. 28, 2016

Related U.S. Application Data

(60) Provisional application No. 61/777,614, filed on Mar. 12, 2013.

(51) Int. Cl.
*G01N 21/77* (2006.01)
(52) U.S. Cl.
CPC ..... *G01N 21/77* (2013.01); *G01N 2021/7759* (2013.01)
(58) Field of Classification Search
CPC ............... G01N 21/77; G01N 33/4875; G01N 2021/7759
See application file for complete search history.

(56) References Cited

U.S. PATENT DOCUMENTS

| 4,217,331 A | 8/1980 | Schaub |
| 4,223,524 A | 9/1980 | Nakagawa |

(Continued)

FOREIGN PATENT DOCUMENTS

| CN | 1427256 A | 7/2003 |
| EP | 1321769 | 6/2003 |

(Continued)

OTHER PUBLICATIONS

European Extended Search Report of European Application No. EP15198651.0 dated Feb. 11, 2016.

(Continued)

*Primary Examiner* — Samuel P Siefke
(74) *Attorney, Agent, or Firm* — Dugan & Dugan, PC

(57) ABSTRACT

The present invention relates to a system, method, and meter for determining the concentration of an analyte in a fluid sample provided on a test strip. The meter (10) may include a body (12), an optical reader (28), and a test strip holder (90). The body (12) has first (14) and second ends (16) and defines a longitudinal axis y extending between the first and second ends (14,16). The optical reader (28) may be coupled to the body (12) and adapted to analyze the analyte on the test strip. The test strip holder (90) may be coupled to the body (12) and include first and second arms (92,94). One of the optical reader (28) or the test strip holder (90) may be movable along the longitudinal axis of the body between a first position, in which the first and second arms (92,94) of the test strip holder (90) overlie the optical reader (28), and a second position, in which the optical reader (28) extends beyond the first and second arms (92,94) of the test strip holder (90). Such configuration allows to push the test strip against the optical reader (28). Pins (58, 60) are also disposed on the test strip holder (90) to grasp the extremities (Continued)

of the test strip and stretch said strip against the optical reader (28).

10 Claims, 9 Drawing Sheets

(56) References Cited

U.S. PATENT DOCUMENTS

| | | |
|---|---|---|
| 4,328,184 A | 5/1982 | Kondo |
| 5,120,420 A | 6/1992 | Nankai et al. |
| 5,194,393 A | 3/1993 | Hugl et al. |
| 5,510,266 A | 4/1996 | Bonner et al. |
| 5,575,403 A | 11/1996 | Charlton et al. |
| 5,630,986 A | 5/1997 | Charlton et al. |
| 5,632,410 A | 5/1997 | Moulton et al. |
| 5,645,798 A | 7/1997 | Schreiber et al. |
| 5,660,791 A | 8/1997 | Brenneman et al. |
| 5,720,924 A | 2/1998 | Eikmeier et al. |
| 5,738,244 A | 4/1998 | Charlton et al. |
| 5,759,364 A | 6/1998 | Charlton et al. |
| 5,798,031 A | 8/1998 | Charlton et al. |
| 5,810,199 A | 9/1998 | Charlton et al. |
| 5,854,074 A | 12/1998 | Charlton et al. |
| 5,856,195 A | 1/1999 | Charlton et al. |
| 5,863,800 A | 1/1999 | Eikmeier et al. |
| 6,428,664 B1 | 8/2002 | Bhullar et al. |
| 6,478,158 B2 | 11/2002 | Gaffney |
| 6,497,845 B1 | 12/2002 | Sacherer |
| 6,534,017 B1 | 3/2003 | Bottwein et al. |
| 6,827,899 B2 | 12/2004 | Maisey et al. |
| 6,988,996 B2 | 1/2006 | Roe et al. |
| 6,997,343 B2 | 2/2006 | May et al. |
| 7,138,089 B2 | 11/2006 | Aitken et al. |
| 7,198,606 B2 | 4/2007 | Boecker |
| 7,211,096 B2 | 5/2007 | Kuhr et al. |
| 7,264,139 B2 | 9/2007 | Brickwood et al. |
| 7,270,247 B2 | 9/2007 | Charlton |
| 7,364,699 B2 | 4/2008 | Charlton |
| 7,449,148 B2 | 11/2008 | Matsumoto et al. |
| 7,549,323 B2 | 6/2009 | Charlton et al. |
| 7,604,592 B2 | 10/2009 | Freeman et al. |
| 7,790,106 B2 | 9/2010 | Uchigaki et al. |
| 7,913,838 B2 | 3/2011 | Zhong |
| 8,105,536 B2 | 1/2012 | Charlton |
| 8,124,014 B2 | 2/2012 | Charlton |
| 8,158,078 B2 | 4/2012 | Chan et al. |
| 8,296,918 B2 | 10/2012 | Alden et al. |
| 8,372,016 B2 | 2/2013 | Freeman et al. |
| 8,574,510 B2 | 11/2013 | Gofman et al. |
| 9,097,700 B2 | 8/2015 | Brown et al. |
| 9,204,829 B2 | 12/2015 | Prais et al. |
| 2002/0057993 A1 | 5/2002 | Maisey et al. |
| 2002/0076349 A1 | 6/2002 | Aitken et al. |
| 2003/0223906 A1 | 12/2003 | McAllister et al. |
| 2004/0178216 A1 | 9/2004 | Brickwood et al. |
| 2005/0201897 A1 * | 9/2005 | Zimmer ............ A61B 10/0045 422/82.05 |
| 2005/0245954 A1 | 11/2005 | Roe et al. |
| 2006/0182656 A1 | 8/2006 | Funke et al. |
| 2007/0007183 A1 | 1/2007 | Schulat |
| 2007/0119710 A1 | 5/2007 | Goldberger et al. |
| 2007/0173739 A1 | 7/2007 | Chan |
| 2007/0173740 A1 | 7/2007 | Chan et al. |
| 2008/0093235 A1 | 4/2008 | Zhong et al. |
| 2008/0094804 A1 | 4/2008 | Reynolds et al. |
| 2008/0118399 A1 | 5/2008 | Fleming |
| 2008/0131322 A1 | 6/2008 | Kheiri et al. |
| 2008/0164164 A1 | 7/2008 | Zhong |
| 2008/0164280 A1 | 7/2008 | Kuriger et al. |
| 2008/0181818 A1 | 7/2008 | Ruan |
| 2008/0190766 A1 | 8/2008 | Rush et al. |
| 2009/0035120 A1 | 2/2009 | List |
| 2009/0074617 A1 | 3/2009 | Uchigaki et al. |
| 2009/0314106 A1 | 12/2009 | Van Halsema |
| 2010/0041156 A1 | 2/2010 | Brenneman et al. |
| 2010/0087754 A1 | 4/2010 | Rush et al. |
| 2010/0129900 A1 | 5/2010 | Clark et al. |
| 2010/0291588 A1 | 11/2010 | McDevitt et al. |
| 2012/0082597 A1 | 4/2012 | Doniger et al. |
| 2013/0048495 A1 | 2/2013 | Charlton |
| 2013/0324822 A1 | 12/2013 | Prais et al. |
| 2015/0004059 A1 | 1/2015 | Brown et al. |
| 2015/0144484 A1 | 5/2015 | Reynolds et al. |
| 2015/0301016 A1 | 10/2015 | Brown et al. |

FOREIGN PATENT DOCUMENTS

| | | | |
|---|---|---|---|
| EP | 1726950 | 11/2006 | |
| EP | 1726951 | 11/2006 | |
| EP | 2426493 | 3/2012 | |
| EP | 2466304 A1 * | 6/2012 | ....... G01N 33/48764 |
| JP | S54-033795 | 3/1979 | |
| JP | S56-175756 | 12/1981 | |
| JP | H06-308115 | 11/1994 | |
| JP | H0921811 A | 1/1997 | |
| JP | 2002-310972 | 10/2002 | |
| JP | 2003-028794 | 1/2003 | |
| JP | 2003-302314 | 10/2003 | |
| JP | 2004-4046 A | 1/2004 | |
| JP | 2006-516328 | 6/2006 | |
| JP | 2006-517651 | 7/2006 | |
| JP | 2007-535388 | 12/2007 | |
| JP | 2007-537454 | 12/2007 | |
| JP | 2008-001428 | 1/2008 | |
| JP | 2008-502901 | 1/2008 | |
| JP | 2008-504532 | 2/2008 | |
| JP | 2008-544266 | 12/2008 | |
| JP | 2012-001256 | 1/2012 | |
| WO | WO 95/13531 | 5/1995 | |
| WO | WO 2001-023885 | 4/2001 | |
| WO | WO2001/063272 | 8/2001 | |
| WO | WO 2002-008753 | 1/2002 | |
| WO | WO 2002-018940 | 3/2002 | |
| WO | WO 2003-042691 | 5/2003 | |
| WO | WO2003/069326 | 8/2003 | |
| WO | WO 2004-063747 | 7/2004 | |
| WO | WO 2005-046477 | 5/2005 | |
| WO | WO 2006-002432 | 1/2006 | |
| WO | WO 2006-019665 | 2/2006 | |
| WO | WO 2006-044850 | 4/2006 | |
| WO | WO 2006-065754 | 6/2006 | |
| WO | WO 2006-076721 | 7/2006 | |
| WO | WO 2007-085438 | 8/2007 | |
| WO | WO 2007-147494 | 12/2007 | |
| WO | WO 2008-111937 | 9/2008 | |
| WO | WO 2009-120664 | 10/2009 | |
| WO | WO 2014/164279 | 10/2014 | |

OTHER PUBLICATIONS

European Extended Search Report of European Application No. 13797254.3 dated Mar. 21, 2016.
Brown et al., of U.S. Appl. No. 15/076,278, titled "Linear, Cartridge-Based Glucose Measurement System," filed Mar. 21, 2016.
Supplementary Partial European Search Report of European Application No. 12859868.7 dated Aug. 5, 2015.
International Search Report and Written Opinion of International Application No. PCT/US2012/070270 dated Feb. 26, 2013.
Taiwan Search Report of Taiwanese Application No. 101148835 dated Oct. 6, 2014.
International Preliminary Report on Patentability of International Application No. PCT/US2012/070270 dated Jul. 3, 2014.
International Search Report and Written Opinion of International Application No. PCT/US2014/021691 dated Sep. 10, 2014.
International Preliminary Report on Patentability of International Application No. PCT/US2014/021691 dated Sep. 24, 2015.
International Search Report and Written Opinion of Application No. PCT/US2012/072118 dated Mar. 28, 2013.
International Search Report and Written Opinion of Application No. PCT/US2013/030897 dated Jun. 27, 2013.
Prais et al., of U.S. Appl. No. 14/943,416, titled "Multistrip Cartridge," filed Nov. 17, 2015.

(56) References Cited

OTHER PUBLICATIONS

International Preliminary Report on Patentability of Application No. PCT/US2013/030897 dated Dec. 2, 2014.
International Preliminary Report on Patentability of Application No. PCT/US2012/072118 dated Dec. 11, 2014.
European Office Action and Search Report European Appication No. 13797254.3 dated Dec. 16, 2015.
Taiwan Search Report of Taiwanese Application No. 104106105 dated Aug. 8, 2016.
Japanese Office Action of Japanese Application No. 2016-500808 dated Nov. 27, 2017.
European Extended Search Report of European Application No. 17198856.1 dated Nov. 27, 2017.

* cited by examiner

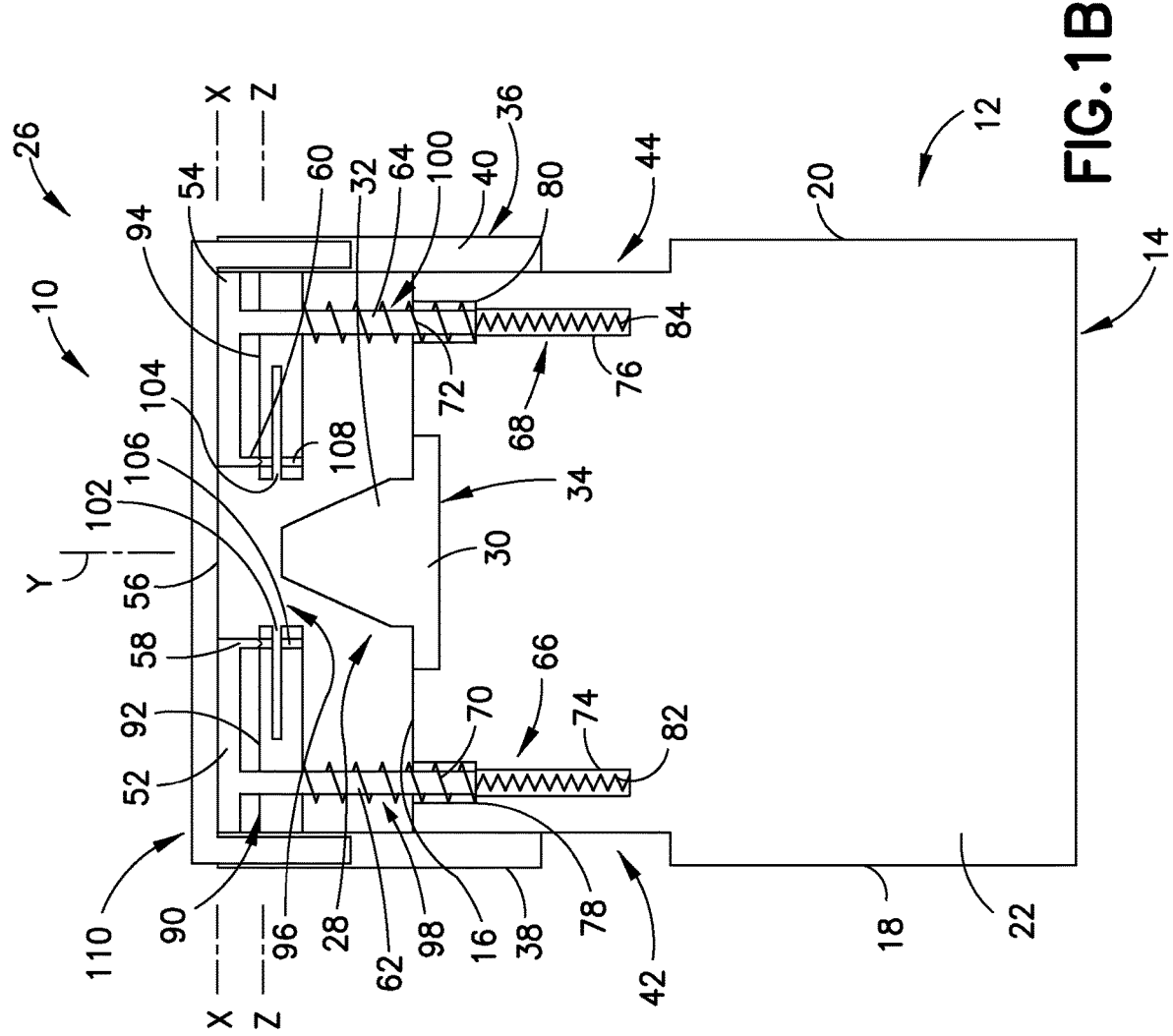
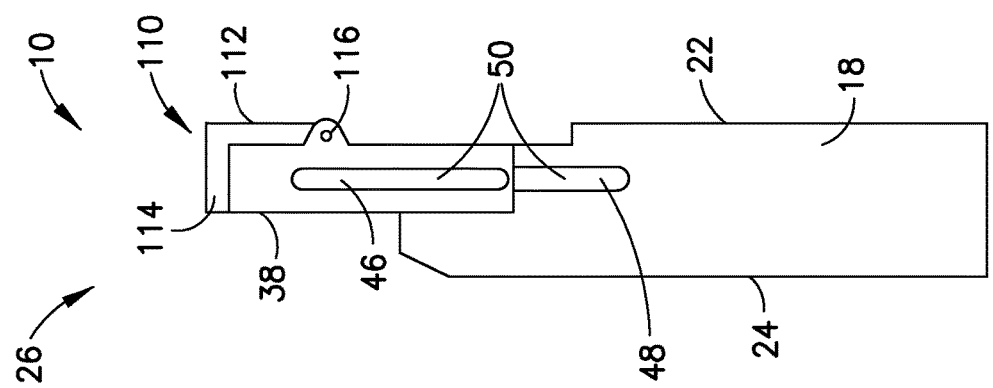

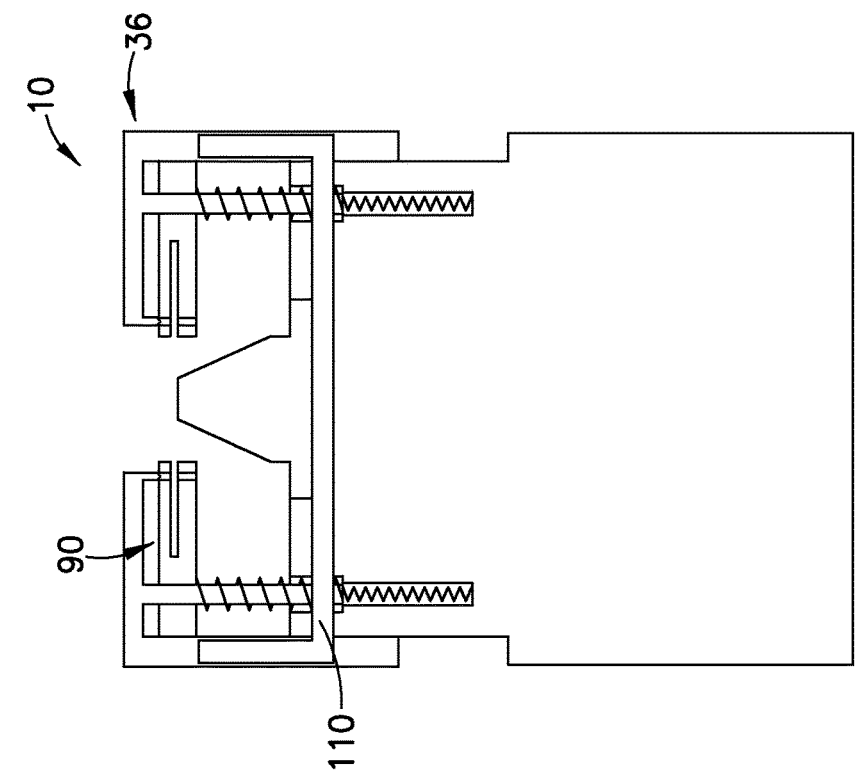
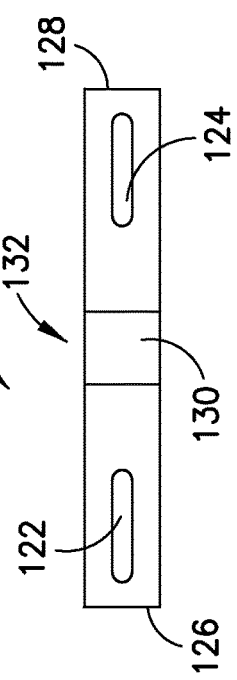
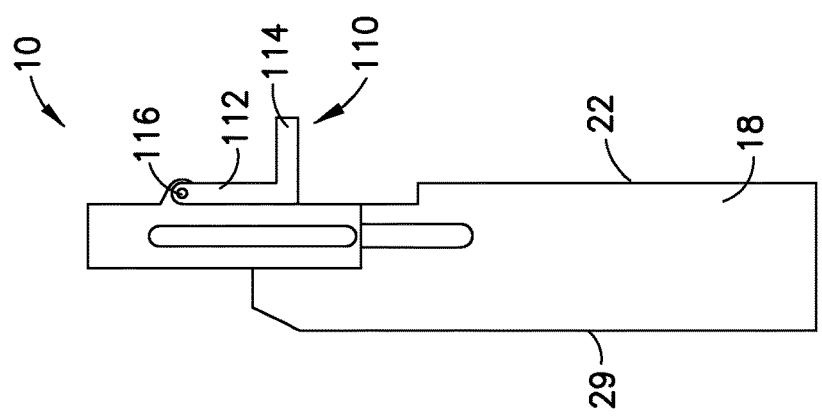
FIG.2B
FIG.3
FIG.2A

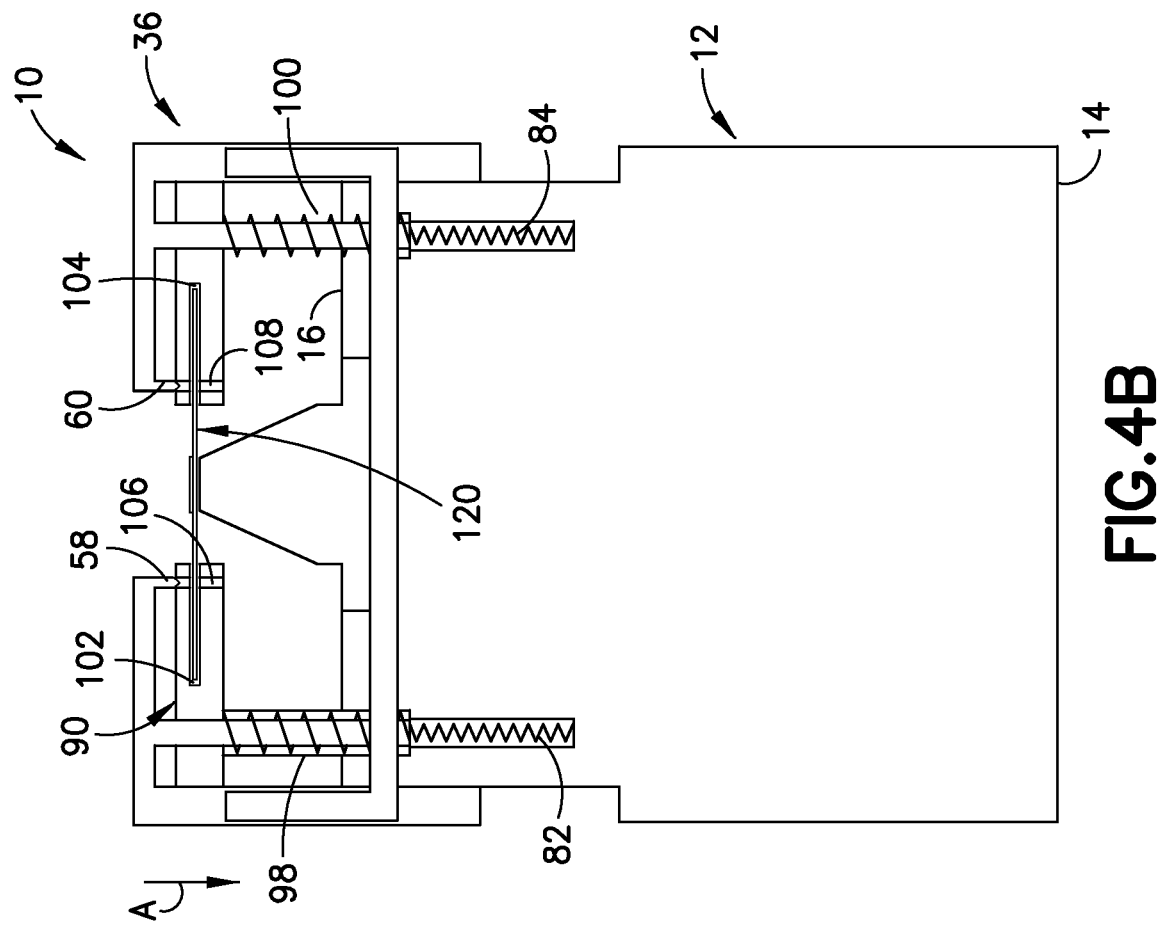
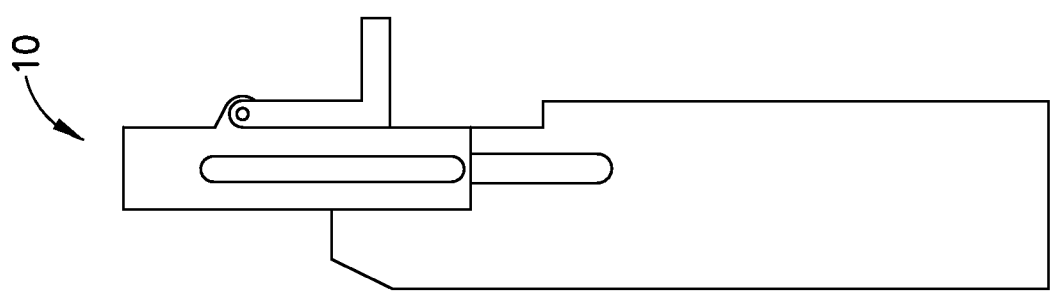

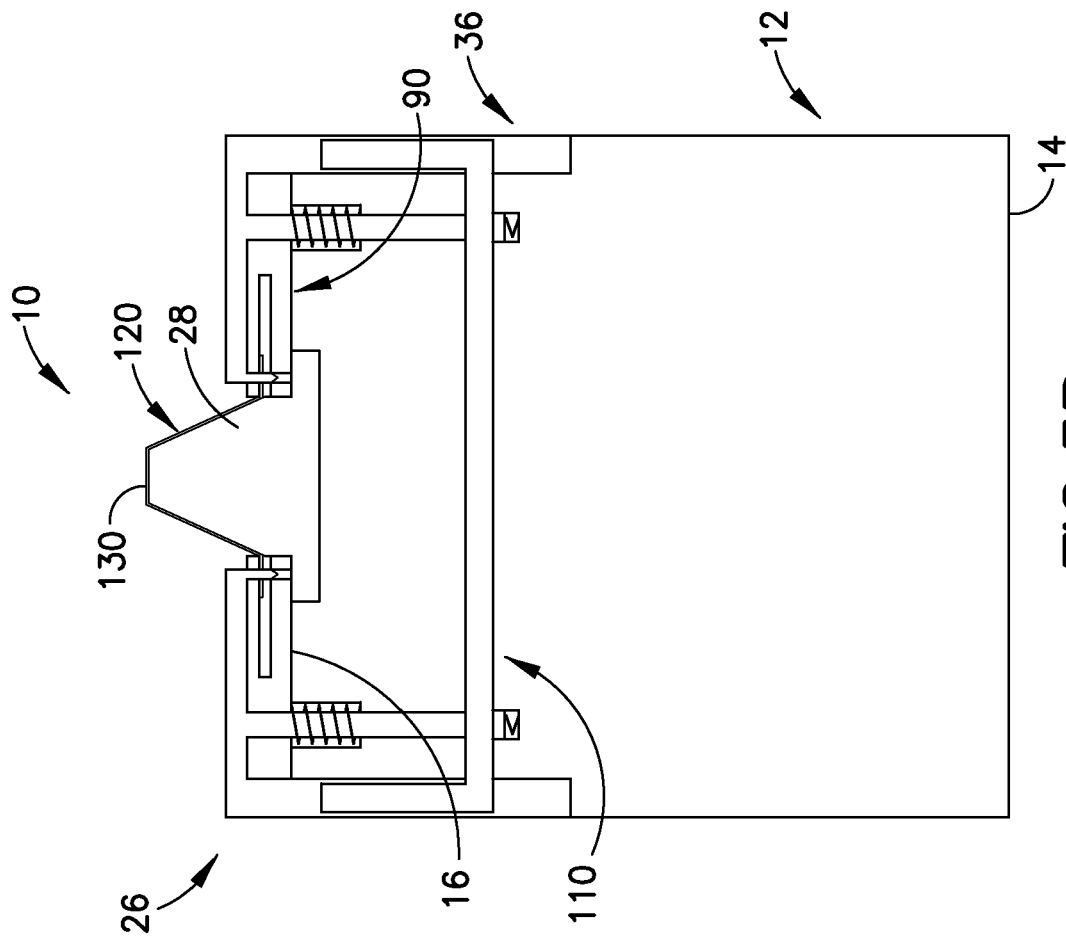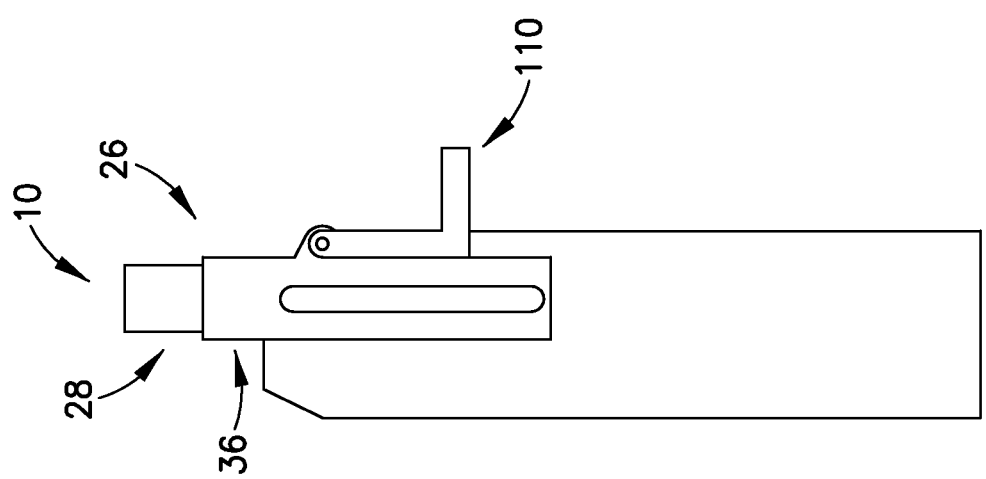

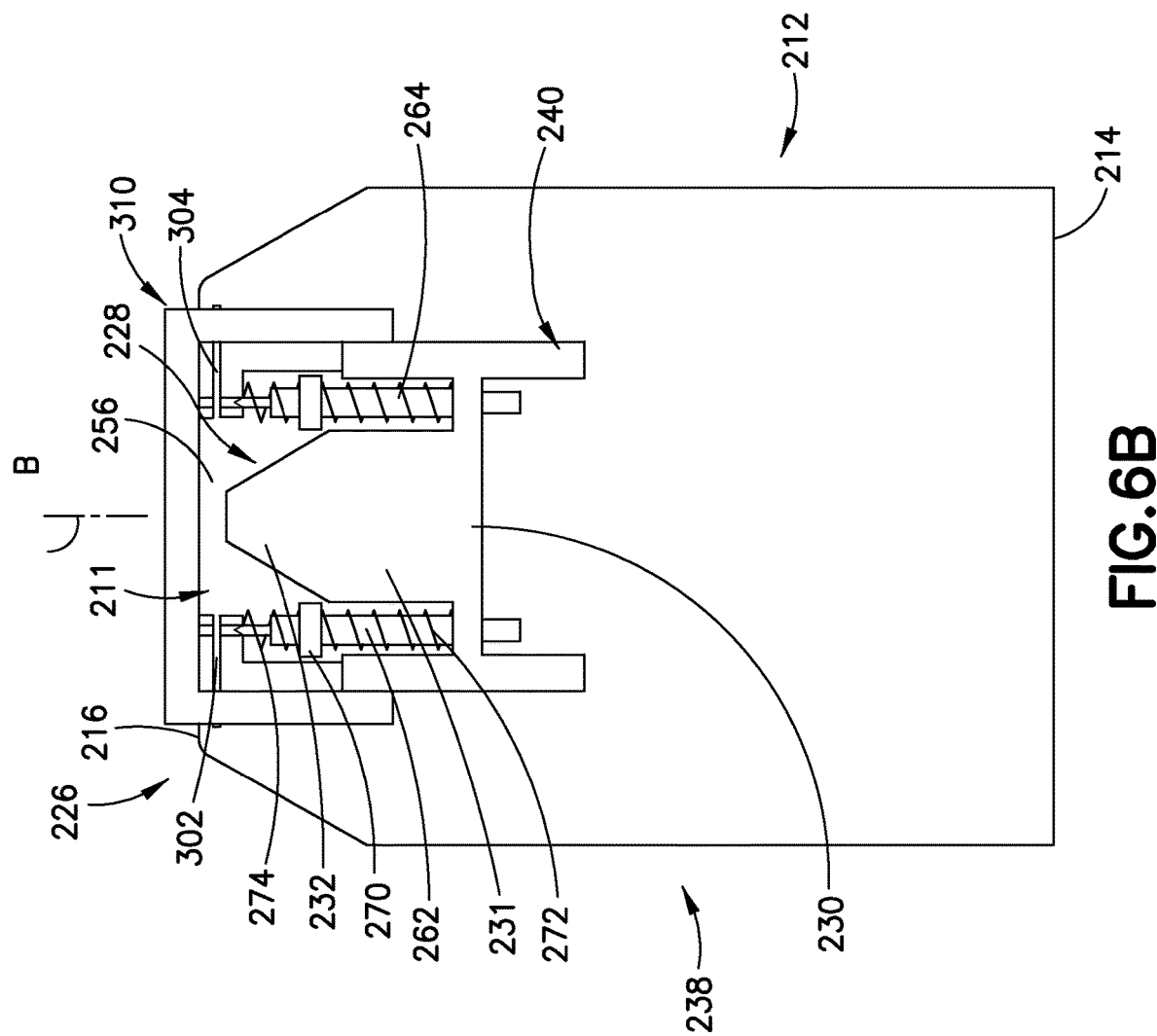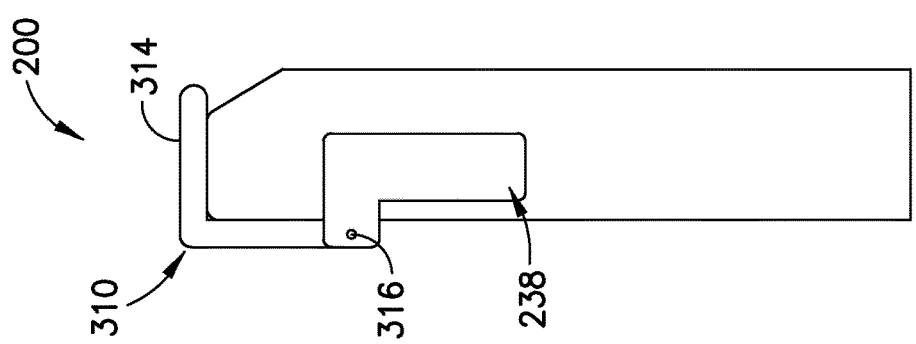

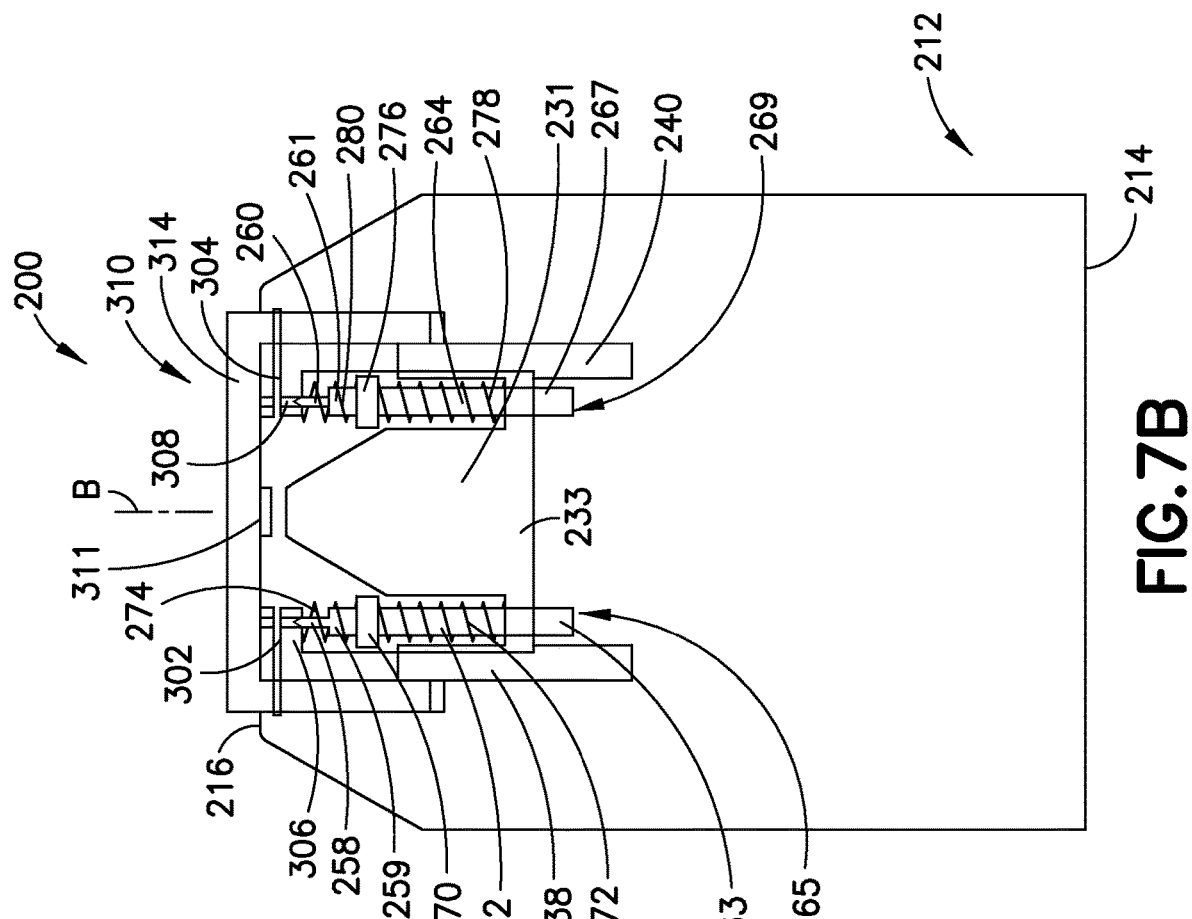
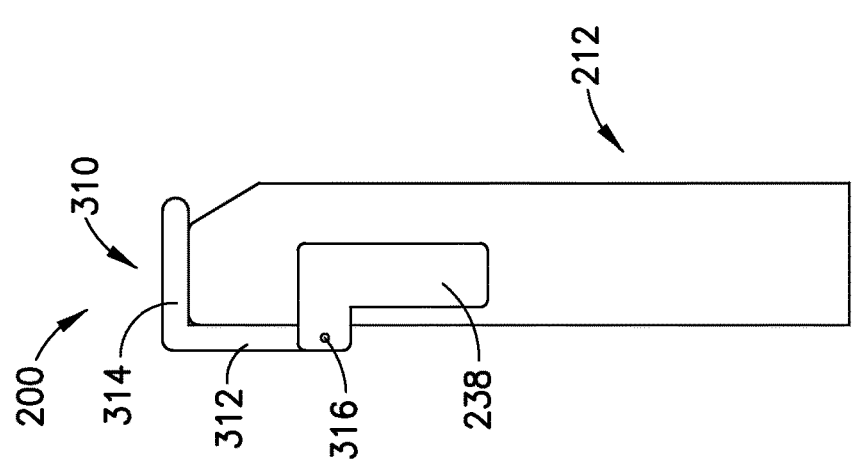

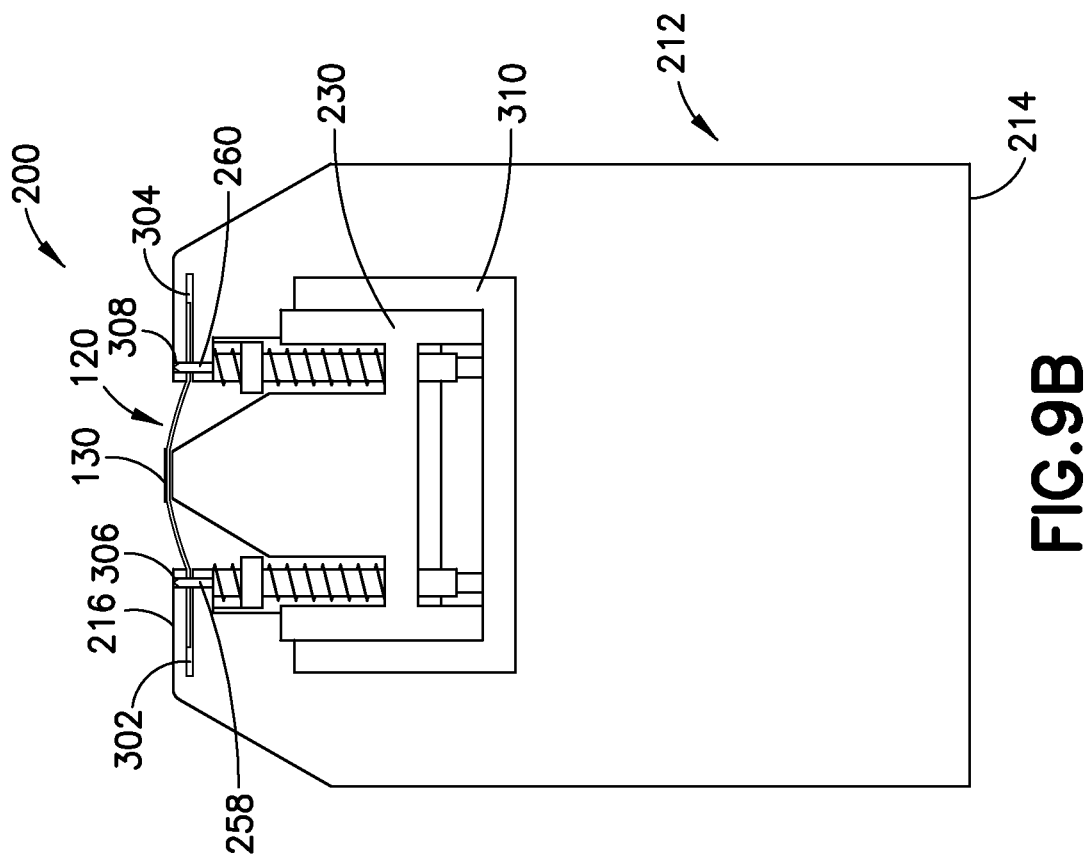
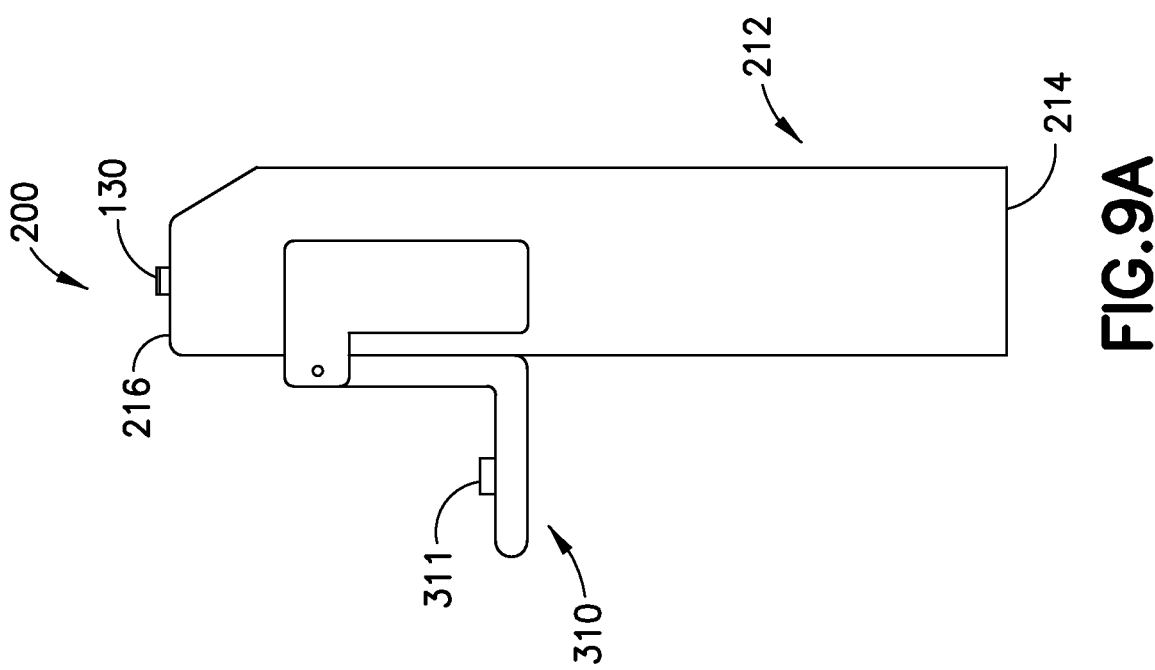

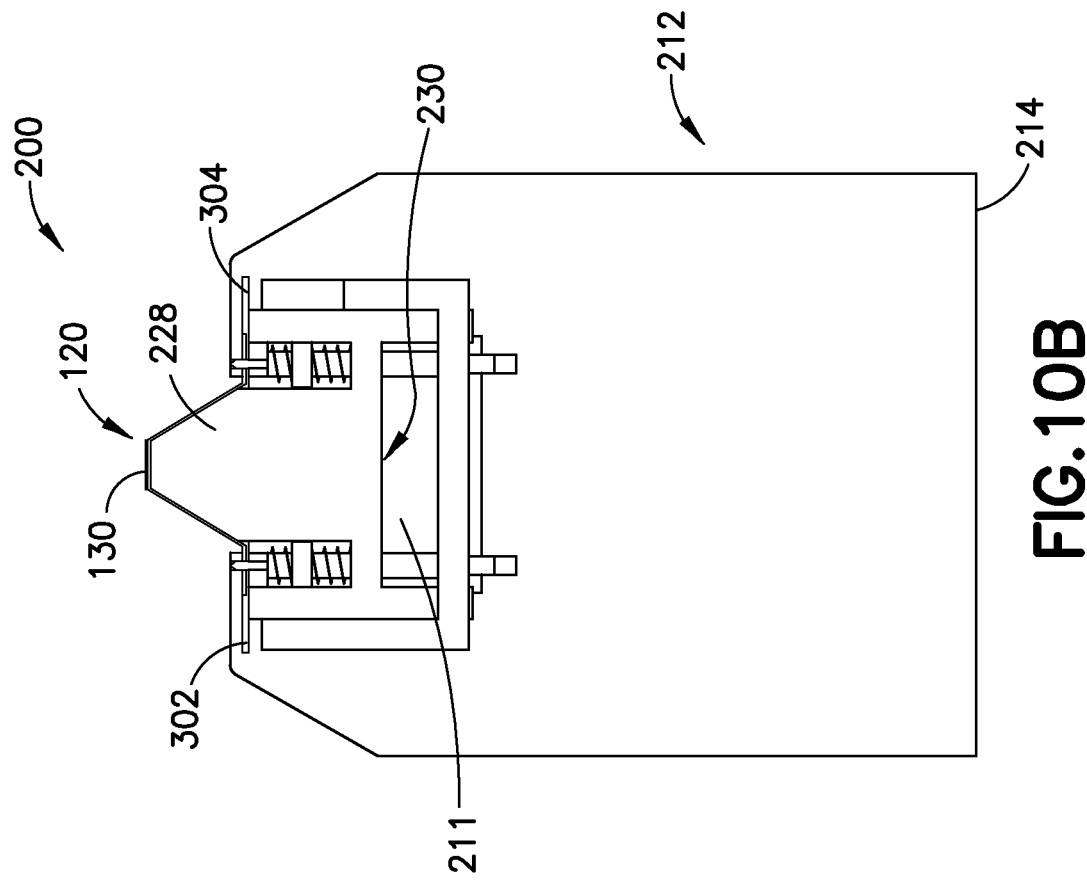
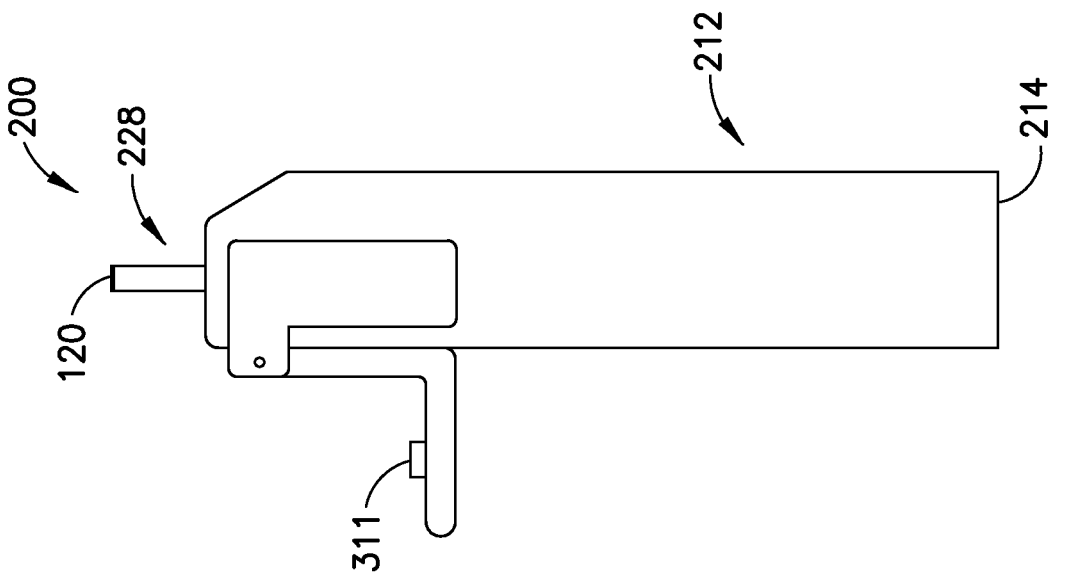

TEST STRIP METER WITH A MECHANISM FOR PUSHING THE TEST STRIP AGAINST AN OPTICAL READER

The present application claims the benefit of the filing date of U.S. Provisional Application No. 61/777,614, filed Mar. 12, 2013, entitled METERS WITH MECHANISM FOR HANDLING SENSORS, the disclosure of which is hereby incorporated herein by reference.

BACKGROUND OF THE INVENTION

The quantitative determination of analytes in body fluids is of great importance in the diagnoses and maintenance of certain physiological abnormalities. For example, lactate, fructosamine, cholesterol, bilirubin, alcohol, and drugs may be monitored or tested in certain individuals. The monitored or tested body fluids may include blood, interstitial fluid, saliva, or urine. In particular, determining glucose in body fluids is important to diabetic individuals who must frequently check the glucose level in their body fluids to regulate the glucose intake in their diets.

One manner of testing glucose levels is through the use of body fluid containers that have reagents included in tape form. These containers, however, have one or more disadvantages. For example, one disadvantage of existing containers is that the test sensors or test strips must be delivered from the container. In such containers, the used sensors are not stored in the container and, thus, may not allow for a convenient and/or safe disposal. Other disadvantages of existing containers include not (a) adequately providing protection against environmental moisture that degrades the reagent and/or (b) keeping the reagent-sensing device adequately clean and protecting it from wear and tear of normal usage.

It would be desirable to provide a container that detects an analyte concentration such as glucose that overcomes the above-noted shortcomings.

BRIEF SUMMARY OF THE INVENTION

The present invention relates to systems and methods for determining the concentration of an analyte in a fluid sample.

In one aspect of the presently disclosed embodiments, the system includes a test strip and a meter.

The test strip has first and second ends, a first end portion adjacent to the first end, a second end portion adjacent the second end, and a central portion between the first and second end portions and remote from the first and second ends. The central portion of the test strip includes a reagent adapted to react with an analyte in a fluid sample and to produce a reaction indicative of the concentration of the analyte in the fluid sample. The first and second ends of the test strip have first and second elongated slots, respectively.

The meter has a body having first and second ends and defining a longitudinal axis extending between the first and second ends. Further, the meter includes a first movable portion movably coupled to the body and movable along the longitudinal axis between a first position, in which the first movable portion is adjacent the first end of the body, and a second position, in which the first movable portion is remote from the second end of the body. The meter also includes a second movable portion movably coupled to the first movable portion and at least partially disposed between the first movable portion and the body. The second movable portion is movable along the longitudinal axis between a first position, in which the first movable portion is adjacent the first end of the body, and a second position, in which the first movable portion is remote from the second end of the body. The second movable portion has first and second arms oriented substantially parallel to each other and spaced apart from one another so as to define a space therebetween. Further, the first and second arms have first and second slots, respectively. Each of the first and second slots is dimensioned to receive at least a portion of the test strip.

The meter further includes a read-head adapted to analyze the reaction between the analyte and the reagent. The read-head has a tapered read portion protruding from the second end of the body. The tapered read portion is at least partially aligned with the space defined between the first and second arms of the second movable portion.

The meter further includes a first spring connected to the first movable portion and biasing the first movable portion to the second position. The first spring is partially disposed within the body and having a first spring constant. The meter also includes a second spring connected to the second movable portion and biasing the second movable portion to the second position. The second spring is partially disposed within the body and has a second spring constant. The first spring constant is less than the first spring constant.

The meter further has a cover pivotably coupled to the first movable portion and movable between a closed position, in which the cover is positioned over the tapered head of the read-head, and an open position, in which the cover is not positioned over the tapered head of the read-head. The cover has a covering portion and connection portion. The covering portion is oriented substantially perpendicular to the connection portion. The meter also has a hinge pivotably connecting the connection portion of the cover to the body.

In another aspect of the presently disclosed embodiments, the system includes a test strip including a reagent adapted to react with an analyte in a fluid sample and to produce a reaction indicative of the concentration of the analyte in the fluid sample and a meter. The meter includes a body having first and second ends. The body of the meter defines a longitudinal axis extending between the first and second ends. Further, meter includes a read-head movably coupled to the body and adapted to analyze the reaction between the analyte and the reagent. The read-head is movable along the longitudinal axis of the body between a first position, in which the read-head is substantially disposed within the body, and a second position, in which the read-head is substantially disposed outside the body.

In another aspect of the presently disclosed embodiments, a meter is disclosed for determining the concentration of an analyte in a fluid sample provided on a test strip. The meter can include a body, a read-head, and a test strip holder. The body has first and second ends and defines a longitudinal axis extending between the first and second ends. The read-head may be coupled to the body and adapted to analyze the analyte on the test strip. The test strip holder may be coupled to the body and include first and second arms. At least one of either the read-head or the test strip holder may be movable along the longitudinal axis of the body between a first position, in which the first and second arms of the test strip holder overlie the read-head, and a second position, in which the read-head extends beyond the first and second arms of the test strip holder. In some embodiments both the read-head and the test strip holder may move along the longitudinal axis. In other embodiments, only the test strip holder or only the read-head may move along the longitudinal axis.

The read-head may be tapered. In one embodiment, the read-head may be frustoconical in shape.

The first and second arms of the test strip holder may be oriented substantially parallel to each other and spaced apart from one another so as to define a space therebetween. The read-head may include a tapered portion that is at least partially aligned with the space defined between the first and second arms.

The read-head may move along the longitudinal axis of the body. When the read-head is in the first position, the read-head may be substantially disposed within the body, and when the read-head is in the second position, the read-head may be substantially disposed outside of the body.

A movable base portion may be coupled to the body. The movable base portion may be movable along the longitudinal axis between a first base position, in which the movable base portion is adjacent the first end of the body, and a second base position, in which the movable base portion is remote from the first end of the body. In some embodiments, the movable base portion may be coupled to the read-head.

A first spring may be partially disposed within the body. The first spring may bias the movable base portion toward the second end. The second spring may be partially disposed within the body and bias the movable base portion toward the first end. The first spring may have a first spring constant that is different than the second spring constant. In one embodiment, the first spring constant may be less than the second spring constant of the second spring.

The test strip holder and the read head may move along the longitudinal axis of the body. The first and second arms of the test strip holder may be oriented substantially parallel to each other and spaced apart from one another so as to define a space therebetween. The read-head may include a tapered portion that is at least partially aligned with the space defined between the first and second arms. In one embodiment, the test strip holder may instead be formed within the body. For example, the test strip holder may be integrally formed with the body, such that the test strip holder does not move relative to the body.

The meter can further include a movable guide portion movably coupled to the body and movable along the longitudinal axis between first and second guide positions. The movable guide portion is in the first guide position when the movable guide portion is remote from the second end of the body. The movable guide portion is in the second position when the movable guide portion is adjacent the second end of the body. The test strip holder may be movably coupled to the movable guide portion and at least partially disposed between the movable guide portion and the body.

In accordance with another aspect of the invention, a method for determining the concentration of an analyte in a fluid sample includes providing the fluid sample on a test strip; positioning the test strip on a first member of a test meter so that a central sample portion of the test strip is aligned with a central portion of a read-head of the test meter; and moving at least one of the first member or the read-head along a longitudinal axis extending between first and second ends of the test meter so that the central portion of the test strip contacts the top surface of the read-head and the peripheral portions of the test strip contact a peripheral edge surface of the read-head extending away from the top surface. The test strip may include a reagent adapted to react with an analyte in the fluid sample and to produce a reaction indicative of the concentration of the analyte in the fluid sample. The central portion of the test strip may be positioned between outer portions of the test strip.

The first member may be moved between a first position, in which the first member is remote from the second end of the body, and a second position, in which the first member is adjacent the second end of the body, the second end of the body being adjacent the read-head.

The read-head may be moved between a first position, in which the read-head is substantially disposed within the body, and a second position, in which the read-head is substantially disposed outside the body.

Another aspect of the presently disclosed embodiments includes a system for determining the concentration of an analyte in a fluid sample. The system includes a test strip and a test meter. The test strip may include a reagent adapted to react with an analyte in a fluid sample and to produce a reaction indicative of the concentration of the analyte in the fluid sample. The meter may include a body having first and second ends. The body may define a longitudinal axis extending between the first and second ends. The meter may further include a read-head movably coupled to the body and adapted to analyze the reaction between the analyte and the reagent. The read-head may be movable along the longitudinal axis of the body between a first position, in which the read-head is substantially disposed within the body, and a second position, in which the read-head is substantially disposed outside the body. In some embodiments, the read-head may have a tapered portion or may be frustoconical in shape.

The body of the meter can further include first and second arms oriented substantially parallel to each other and spaced apart from one another so as to define a space therebetween. The read-head may be at least partially aligned with the space defined between the first and second arms of the body.

The first and the second arms of the test strip holder may have first and second slots, respectively. Each of the first and second slots can be dimensioned to receive at least a portion of the test strip. The first and second slots may be oriented substantially perpendicular to the longitudinal axis.

The meter may further comprise a movable base portion coupled to the body and the read-head. The movable base portion may be movable along the longitudinal axis between a first base position, in which the movable base portion is adjacent the first end of the body, and a second base position, in which the movable base portion is remote from the first end of the body. When the movable base portion is in the first base position, the read-head is in the first position. When the movable base portion is in the second base position, the read-head is in the second position.

The system may further include a first spring and a second spring. The first spring may be partially disposed within the body, the first spring biasing the movable base portion toward the second end and having a first spring constant. The second spring may be partially disposed within the body and bias the movable base portion toward the first end. The second spring may have a second spring constant and the first spring constant may be less than the second spring constant.

These and other embodiments of the present disclosure are more fully described hereinbelow.

BRIEF DESCRIPTION OF THE DRAWINGS

Various embodiments of the present invention will now be described with reference to the appended drawings. It is appreciated that that these drawings depict only exemplary embodiments of the invention and are therefore not to be considered limiting of its scope.

FIG. 1A is a schematic side view of a meter for determining the concentration of an analyte in a fluid sample according to an embodiment of the present invention;

FIG. 1B is a schematic front view of the meter of FIG. 1A;

FIG. 2A is a schematic side view of the meter of FIG. 1A with a cover in an open position;

FIG. 2B is a schematic front view of the meter of FIG. 1A with the cover in an open position;

FIG. 3 is a schematic top view of a test strip for use with the meters described in the present invention;

FIGS. 4A, 4B, 5A, and 5B illustrate steps for operating the meter shown in FIG. 1A;

FIG. 6A is a schematic side view of a meter for determining the concentration of an analyte in a fluid sample according to an embodiment of the present invention;

FIG. 6B is a schematic front view of the meter shown in FIG. 6A; and

FIGS. 7A, 7B, 8A, 8B, 9A, 9B, 10A, and 10B illustrate steps for operating the meter shown in FIG. 6A.

DETAILED DESCRIPTION

Figure 8B:
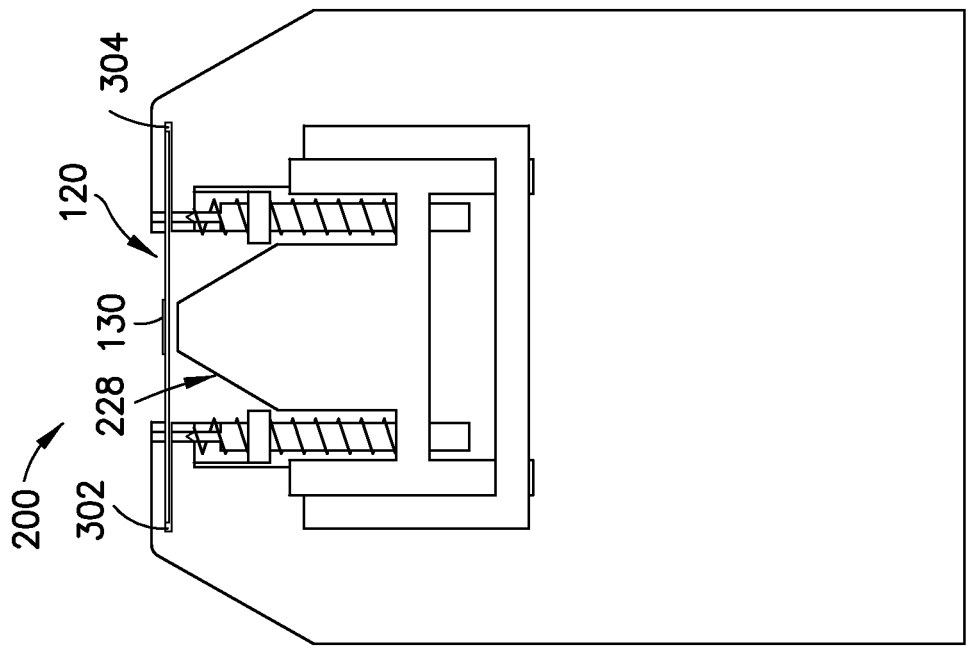

The present invention relates to systems, meters, and methods for reading and handling test strips, such a test strips. FIGS. 1A and 1B depict an embodiment of a meter 10 for reading and handling test strips adapted for determining the analyte concentration level in a fluid sample. Although the following discussion describes the use of test strips for determining the glucose concentration in blood, the presently disclosed meter 10 may contain test strips designed to determine the concentration of other analytes in other types of samples. For example, test strips may alternatively measure glucose, lipid profiles (e.g., cholesterol, triglycerides, low-density lipoprotein (LDL) and high-density lipoprotein (HDL)), microalbumin, hemoglobin A1c, fructose, lactate, bilirubin, or other analytes. The analytes may be in, for example, a whole blood sample, a blood serum sample, a blood plasma sample, or body fluids like interstitial fluid (ISF) and urine.

The meter 10 includes a body 12 having a first end 14, a second end 16, and defining a longitudinal axis Y. The longitudinal axis Y passes through the first and second ends 14 and 16 of the body 12. The body 12 further has oppositely facing first and second sidewalls 18 and 20 and front and rear walls 22 and 24. The first and second sidewalls 18 and 20 and the front and rear walls 22 and 24 extend between the first and second ends 14 and 16 of the body 12.

In addition to the body 12, the meter 10 includes a read-head 28 adapted to analyze the reaction between the analyte and the reagent on a test strip. The read-head 28 may be an optical read-head configured to illuminate a reagent pad (specimen) on a test strip and obtain the measurement of nonspecular reflected light. The read-head 28 is mounted on the second end 16 of the body 12 and may include a substantially planar base 30 and a substantially tapered or frustoconical read portion 32. The substantially planar base 30 of the read-head 28 may be disposed within a slot 34 of the body 12. The slot 34 of the body 12 may be located within a substantially central portion of the second end 16 remote from the first and second sidewalls 18 and 20. The substantially planar read portion 32 of the read-head 28 protrudes away from the second end 16 of the body 12 in a direction opposite of the first end 14 of the body along the longitudinal axis Y.

The meter 10 further includes a mechanism 26 for handling test strips, such as test strips and sensors in a tape form. The handling mechanism 26 includes a first movable member 36 movably coupled to the body 12. The first movable member 36 can move relative to the body 12 along the longitudinal axis Y between a first position and second position. In the first position, the first movable member 36 is remote from the second end 16 of the body 12, as shown in FIG. 1B. In the second position, the first movable member 36 is adjacent the second end 16 of the body 12, as illustrated in FIG. 5B.

The first movable member 36 may include first and second sliding arms 38 and 40 adapted to slide along the sidewalls 18 and 20 of the body 12, respectively. Specifically, the first sliding arm 38 can slide along a recess 42 formed on at least a portion of the first sidewall 18 of the body 12. Similarly, the second sliding arm 40 can slide along a recess 44 formed on at least a portion of the second sidewall 20 of the body 12. Each of the first and second sliding arms 38 and 40 may include a first sliding rail 46 adapted to slide along a second sliding rail 48 disposed along the sidewall (18 or 20). The sliding rails 46 and 48 collectively form a guiding mechanism 50 adapted to guide the movement of the sliding arm (38 or 40) along the sidewall (18 or 20). The meter 10 may alternatively include other kinds of guiding mechanisms capable of guiding the movement of the sliding arms 38 and 40 relative to the sidewalls 18 and 20 of the body 12.

The first movable member 36 further includes first and second securing arms 52 and 54 adapted to secure a test strip to a second movable member, as discussed in detail below. The first securing arm 52 extends substantially perpendicular from the first sliding arm 38 toward the read-head 28. The second securing arm 54 extends substantially perpendicular from the second sliding arm 40 toward the read-head 28. The first and second securing arms 52 and 54 are substantially parallel to each other and may span along a common longitudinal axis X. However, the first and second securing arms 52 and 54 are spaced apart from each other so as to form a space 56 or aperture therebetween. The space 56 is dimensioned to receive at least a portion of the read-head 28.

The first and second securing arms 52 and 54 include securing pins 58 and 60, respectively. Each of the securing pins 58 and 60 may have a tapered configuration and extend substantially perpendicular from an end of the respective securing arm 52 or 54 adjacent to the space 56. As discussed in detail below, the securing pins 58 and 60 aid in securing a test strip to the meter 10.

The first movable member 36 further includes first and second elongated members 62 and 64, such as tubes or rods, partially positioned within the body 12. The first and second elongated members 62 and 64 may have any suitable cross-section, such as square, circular, oval, etc. The first elongated member 62 extends substantially perpendicular from the first securing arm 52, while the second elongated member 64 extends substantially perpendicular from the second securing arm 54. The first elongated member 62 is dimensioned to be slidably positioned within a first elongated opening or bore 66 of the body 12. The second elongated member 64 is dimensioned to be slidably positioned within a second elongated opening or bore 68 of the body 12.

The first and second elongated openings 66 and 68 are substantially parallel to each other and each extends from the second end 16 of the body 12 to a location between the first and second ends 14 and 16 of the body 12. Each of the first and second elongated openings 66 and 68 has a respective first portion 70 and 72 adjacent to the second end 16 of the body 12 and a respective second portion 74, 76 remote from the second end 16 of the body 12. The cross-sectional area or diameter of the first portion 70 of the opening 66 is larger than the cross-sectional area of the second portion 74. Similarly, the cross-sectional area of the first portion 72 of the opening 68 is larger than the cross-sectional area of the second portion 76. A shoulder 78 may divide the first and second portions 70 and 74 of the opening 66. Likewise, a shoulder 80 may divide the first and second portions 72 and 76 of the opening 68.

The handling mechanism 26 further includes a biasing member, such as a spring 82, for biasing the first movable member 36 toward its first position remote from the second end 16 of the body 12. The spring 82 is connected to the first elongated member 62 and may be disposed within the second portion 74 of the opening 66. Thus, the second portion 74 of the opening 66 is dimensioned to receive the spring 82.

The handling mechanism 26 includes another biasing member, such as a spring 84, for biasing the first movable member 36 toward its first position remote from the second end 16 of the body 12. The spring 84 is connected to the second elongated member 64 and is disposed within the second portion 76 of the opening 68. Hence, the second portion 76 of the opening 68 is dimensioned to receive the spring 84.

The handling mechanism 26 further includes a second movable member 90 connected to the body 12 and movable along the longitudinal axis Y between a first position remote from the second end 16 of the body 12 (FIG. 1A) and a second position adjacent the second end 16 of the body 12 (FIG. 5B). The second movable member 90 can move independently of the first movable member 36 and includes first and second arms 92 and 94 adapted to hold a test strip, such as a test strip. Despite this independent motion capability, the second movable member 90 may abut the first movable member 36 at least when located in its second position.

The first and second arms 92 and 94 of the second movable member 90 are oriented substantially parallel to each other and may be positioned along a common longitudinal axis Z. However, the first and second arms 92 and 94 are spaced apart from each other so as to form a space or aperture 96 therebetween. The space 96 is dimensioned to receive at least a portion of the read-head 28.

The first arm 92 of the second movable member 90 may be attached to the body 12 via a biasing member, such as spring 98, at least partially disposed within the first portion 70 of the opening 66. An end of the spring 98 may rest on (or be mounted on) the shoulder 78 of the opening 66. The spring 98 is stronger or stiffer than spring 82. In other words, the spring constant (according to Hooke's law of elasticity) of spring 98 is higher than the spring constant of spring 82. Thus, the first movable member 36 displaces a larger distance toward the second end 16 of the body 12 relative to the displacement of the second movable member 90 upon application of the same force to first and second movable members 36 and 90.

The second arm 94 of the second movable member 90 may be attached to the body 12 via a biasing member, such as spring 100, at least partially disposed within the first portion 72 of the opening 68. An end of the spring 100 may rest on (or be mounted on) the shoulder 80 of the opening 68. The spring 100 is stronger or stiffer than spring 84. In other words, the spring constant (according to Hooke's law of elasticity) of spring 100 is higher than the spring constant of spring 84. Thus, the first movable member 36 displaces a larger distance toward the second end 16 of the body 12 relative to the displacement of the second movable member 90 upon application of the same force to first and second movable members 36 and 90.

Each of the first and second arms 92 and 94 of the second movable member 90 has slots 102 and 104, respectively. Each of the slots 102 and 104 is dimensioned to receive at least a portion of a test strip, such as a test strip, and may extend along longitudinal axis Z. Each of the first and second arms 92 and 94 further has respective holes 106 and 108. The holes 106 and 108 are dimensioned to receive securing pins 58 and 60, respectively. The holes 106 and 108 may be oriented substantially orthogonal to the longitudinal axis Z and substantially parallel to the longitudinal axis Y.

The meter 10 further includes a lid or cover 110 pivotally coupled to the handling mechanism 26. The cover 110 can move between a closed position (FIG. 1A), in which the cover is positioned over the read-head 28, and an open position (FIG. 2A), in which the cover is not positioned over the read-head 28. The cover 110 may include connection portion or lip 112 pivotally connected to the first movable member 36 and a covering portion 114 extending substantially perpendicular from an end of the connection portion 112. The covering portion 114 overlies the read-head 28 when the cover 110 is in the closed position and therefore protects the read-head 28 from environmental contamination. A hinge 116 or any other device or mechanism suitable for establishing a pivotal connection couples the connecting portion 114 of the cover 110 to the first movable member 36 of the handling mechanism 26. These pivotal connections allow the cover 110 to move between a closed position (FIG. 1A), in which the covering portion 114 overlies the read-head 28 and therefore protects the read-head from environmental contamination, and an open position (FIG. 2A, 2B), in which the covering portion does not overlie the read-head 28.

FIG. 3 shows a test strip or test strip 120 for use with meter 10. In some embodiments, the test strip 120 may be a top fill test strip. In other embodiments, the test strip 120 may be other types in tape form. In the embodiment shown in FIG. 3, the test strip 120 defines a longitudinal axis A along its length and may have first and second elongated slots 122 and 124 substantially in-line with each other. Both elongated slots 122 and 124 extend through the thickness of the test strip 120 and may be positioned along the longitudinal axis A. The first elongated slot 122 is adjacent the first end 126 of the test strip 120, whereas the second elongated slot 124 is adjacent the second end 128 of the test strip 120. The test strip 120 also has a reaction area 130 containing one or more reagents for reacting with an analyte of interest in a fluid sample. The reaction area 130 is located within a central region 132 of the test strip 120 remote from the first and second ends 126 and 128. In one example, the test strip 120 may be 28.3 millimeters long and 4 millimeters wide. The test strip 120 may also be dimensioned differently.

In operation, the test strip 120 and the meter 10 collectively form a system for determining the concentration of an analyte in a fluid sample. Initially, the cover 110 of the meter 10 may be in a closed position, as shown in FIGS. 1A and 1B. Before placing the test strip 120 in the meter 10, the cover 110 is moved from the closed position to the open position, as seen in FIGS. 2A and 2B, to uncover the second movable member 90. The cover 110 may be moved to the open position by pivoting it 180 degrees as seen in FIGS. 2A and 2B. With the cover 110 in its open position, the test strip 120 is placed within the slots 102 and 104 of the second movable member 90, as shown in FIGS. 4A and 4B.

With continued reference to FIGS. 4A and 4B, the first and second movable members 36 and 90 are then moved from their first position toward their second position by urging or pushing the first and second movable members toward the second end 16 of the body 12 along arrow A. A user may urge the first and second movable members 36 and 90 toward their second position through application of force on the cover 110. While moving the first and second movable members 36 and 90 from the first position to the second position, the first movable member approaches the second movable member 90 because the springs 82 and 84 are weaker than the springs 98 and 100 connected to the second movable member. As a result, the securing pins 58 and 60 of the first movable member 36 can pass through the holes 106 and 108 of the second movable member 90 and the slots 122 and 124 of the test strip 120 while the first and second movable members move from the first to the second position, thereby securing the test strip to the meter 10, as seen in FIGS. 5A and 5B.

As seen in FIGS. 5A and 5B, continued movement of the first and second movable members 36 and 90 toward the second end 16 of the body 12 urges the reaction area 130 of the test strip 120 against the read-head 28 of the meter 10. Also, while moving the first and second movable members 36 and 90 from the first position to the second position, the securing pins 58 and 60 slide outwardly along the slots 122 and 124 of the test strip 120 toward the ends 126 and 128 of the test strip 120. When the securing pins 58 and 60 reach the outward ends of the slots 122 and 124 of the test strip 120, the test strip 120 is maintained in tension and the reaction area 130 of the test strip 120 is pressed against the read-head 28 of the meter 10.

The first and second movable members 36 and 90 may be secured in their second position adjacent the second end 16 of the body with any suitable securing mechanism or device (not shown). In one exemplary embodiment, the securing mechanism includes a latch attached to the cover 110 and spring-loaded catch attached adjacent the first end 14 of the body 12.

Once the first and second movable members 36 and 90 are in their second positions, as shown in FIGS. 5A and 5B, a fluid sample may be deposited on the reaction area 130 of the test strip 120 to determine the concentration of an analyte in that fluid sample in the conventional manner. After testing the fluid sample, the test strip 120 can be removed from the second movable member 90 before moving the cover 110 back to its closed position. Alternatively, the cover 110 may be moved to its closed position with the test strip 120 with the test strip inside the meter 10. In this case, the test strip 120 may be disposed of at a later time.

In the embodiment described above, the read-head 28 remains stationary relative to the body 12 of the meter 10, while the test strip 120 moves toward the read-head. In other embodiments, however, the read-head moves toward the test strip, while the test strip remains stationary relative to the body of the meter.

FIGS. 6A-7B illustrate meter 200 having handling mechanism 226 that allows a read-head 228 to move relative to the test strip 120, while the test strip remains stationary relative to the body 212 of the meter 200. The body 212 of the meter 200 defines a longitudinal axis B along its length. The longitudinal axis B extends between oppositely facing first and second ends 214 and 216 of the body 212.

The body 212 of the meter 200 has first and slots 302 and 304 adjacent its second end 216. Each of the slots 302 and 304 is dimensioned to receive at least a portion of the test strip 120. The first and second slots 302 and 304 may be oriented substantially perpendicular to the longitudinal axis B and are spaced apart from each other so as to form a space or opening 256 therebetween. The opening 256 leads to an open cavity 211 of the body 212. The open cavity 211 is dimensioned to receive at least a portion of the handling mechanism 226 and the read-head 228.

The body 212 of the meter 200 further has holes 306 adjacent the slot 302 and holes 308 (FIG. 7B) adjacent the slot 304. The holes 306 and 308 may be substantially parallel to the longitudinal axis B.

The read-head 228 is dimensioned to fit within the open cavity 211 and includes a substantially tapered or frusto-conical read portion 232 and a substantially cylindrical portion 231. In some embodiments, the read-head 228 may be an optical read-head configured to illuminate a reagent pad (specimen) on a test strip and obtain the measurement of nonspecular reflected light. Moreover, the read-head 228 is mounted on a support base 230 and can move relative to the body 212 of the meter 200 along the longitudinal axis B. The read-head 228 is fixed to the support base 230 and therefore moves in unison with the support base.

The support base 230 is part of the handling mechanism 226 and can move along the longitudinal axis B between a first position, in which the read-head 228 is entirely or substantially disposed within the open cavity 211, as seen in FIG. 6B, and a second position, in which the entire or a substantial portion of the read portion 232 of the read-head 228 is positioned outside the open cavity 211, as shown in FIG. 10B. Further, the support base 230 may include a support portion 233 having a substantially flat bottom surface and first and second elongated support members 238 and 240. The substantially flat bottom surface of the support portion 233 may be oriented substantially orthogonal to the longitudinal axis B. The first and second elongated support members 238 and 240 may each have a substantially L-shape, as seen in FIG. 7A.

Figure 8A:
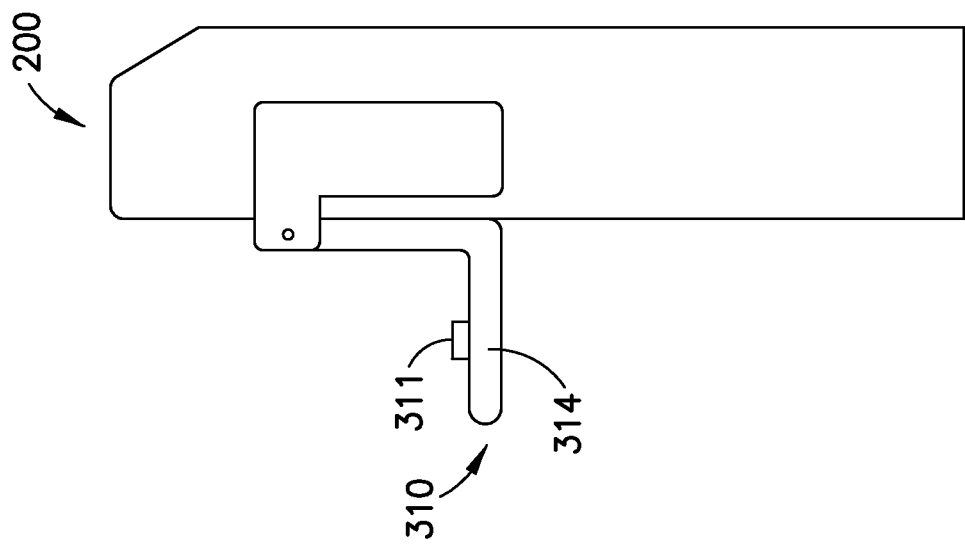

The meter 200 further includes lid or cover 310 pivotally coupled to the first and second elongated support members 238 and 240. The cover 310 may include a lip or connection portion 312 pivotally connected to the first and second elongated support members 238 and 240 and covering portion 314 extending substantially perpendicular from an end of the connection portion 312. In one embodiment, a hinge 316 may pivotally connect an end of the first elongated support member 238 to an end of the cover 310. Similarly, a hinge (not shown) may pivotally connect an end of the second elongated support member 240 to another end of the cover 310. Although the figures depict hinges pivotally connecting the cover 310 to the first and second elongated support members 238 and 240, any suitable device or mechanism, such as a pivot pin, may pivotally couple the cover to the first and second elongated support members. These pivotal connections allow the cover 310 to move between a closed position as shown in FIG. 7A, in which the covering portion 314 overlies the read-head 228 and therefore protects the read-head from environmental contamination, and an open position as seen in FIG. 8A, in which the covering portion does not overlie the read-head.

A calibration or reference standard 311 may be attached to an inner portion of the cover 310. The calibration standard may face the read-head 228 and can provide a known reflectance level for calibrating or checking that the optics are clean and not contaminated with blood or any other fluid. If the reaction sequence does not allow the standard to be measured before the test (e.g., blood glucose test), it can be measured after the next analysis.

The handling mechanism 226 includes first and second guiding elongated members 262 and 264 along which the support base 230 can slide. The support base 230 may be a substantially H-shaped. The first and second guiding elongated members 262 and 264 may be a tube or a rod or any other type of elongated structure. The cross-section of the first and second elongated members 262 and 264 may have different shapes, such as oval, square, rectangular, circular, etc. Regardless, the first and second elongated members 262 and 264 can move along the longitudinal axis B and the read-head 228 can move along the guiding members 262 and 264 of the meter 200. In some embodiments, the first and second guiding elongated members 262 and 264 may be spaced apart and substantially parallel to each other. The first end 263 of the first guiding elongated member 262 is dimensioned to be positioned and slide within an opening or bore 265 of the body 212. Similarly, the first end 267 of the second guiding elongated member 264 is dimensioned to be positioned and slide within an opening or bore 269 of the body 212. The openings 265 and 269 are in communication with the open cavity 211.

Body hole opening 302 is smaller than the diameter of second end of the first guiding elongated member 262 and thus limits movement of elongated member 262 towards second end. A first securing pin 258 may have a tapered tip and protrudes from the second end 259 of the first guiding elongated member 262 toward the second end 216 of the body 212. Moreover, the first securing pin 258 is dimensioned to be received within the holes 306 of the body 212 to secure at least a portion of a test strip 120 positioned in the slots 302 and 304.

Body hole opening 308 is smaller than the diameter of second end of the first guiding elongated member 264 and thus limits movement of elongated member 262 towards second end. A second securing pin 260 may have a tapered tip and protrudes from the second end 261 of the second guiding elongated member 264. In addition, the second securing pin 260 is dimensioned to be received within the holes 308 to secure at least a portion of a test strip 120 positioned in the slots 302 and 304.

A first mechanical stop or divider 270 is disposed around the outer periphery of the first guiding elongated member 262 adjacent the second end 259. Further, the first mechanical stop 270 separates a first biasing element or spring 272 from a second biasing element or spring 274. The first and second spring 272 and 274 may be both positioned around the first guiding elongated member 262. The second spring 274 biases the first guiding elongated member toward the first end 214 of the body 212, whereas the first spring 272 biases the support base 230 toward the second end 216 of the body. The first spring 272 is stiffer than the second spring 274.

A second mechanical stop or divider 276 is disposed around the outer periphery of the second guiding elongated member 264 adjacent the second end 261. Moreover, the second mechanical stop 276 separates a third biasing element or spring 278 from fourth biasing element or spring 280. The third and fourth springs 278 and 280 may be both positioned around the second guiding elongated member 264. The fourth spring 280 biases the second guiding elongated member 264 toward the first end 214 of the body 212, while the third spring 278 biases the support base toward the second end 216 of the body 212. The third spring 278 is stiffer than the fourth spring 280.

In use, the meter 200 can be used to handle a test strip or test strip 120. During operation, the cover 310 is moved from the closed position, as seen in FIG. 7A, to the open position, as shown in FIG. 8A, to expose the slots 302 and 304 and the read-head 228. The test strip 120 is then placed within the slots 302 and 304, as depicted in FIG. 8B.

Once the test strip 120 has been placed within the slots 302 and 304, the support base 230 is urged away from the first end 214 of the body 212 against the influence of the first and second springs 272 and 274, and third and fourth springs 278 and 280 (i.e., toward its second position) as seen in FIGS. 9A and 9B. The support base 230 may be moved via the cover 310. While the support base 230 moves toward its second position, the read-head 228 moves toward the test strip 120 against springs one, two three and four. As second and fourth springs 274 and 280 are weaker than first and second springs 272 and 278, first and second guiding elongated members 262 and 264 move first towards second end 216 where the first and second securing pins 258 and 260 enter holes 306 and 308, respectively. Movement of first guiding elongated member 262 ceases when second end 259 is excluded by the smaller opening of hole 308. Movement of second guiding elongated member 264 ceases when second end 261 is excluded by the smaller opening of hole 308. Continued movement of the support base 230 away from the first end 214 of the body causes the read-head 228 to slide along first and second guiding elongated member 262 and 264 against first and third springs 272 and 278 and push at least the reaction area 130 of the test strip 120 past the second end 216 of the body 212, as shown in FIGS. 9A and 9B.

As the first and second securing pins 258 and 260 enter holes 306 and 308, respectively, the first and second securing pins 258 and 260 pass through slots 122 and 124 of the test strip 120, thereby securing the test strip to the meter 200. While the support base 230 continues to move away from the first end 214 of the body 212, the first and second securing pins 258 and 260 move along the slots 122 and 124 of the test strip 120 from the inner ends of the slots to the outer ends of the slots. The support base 230 should be moved away from the first end 214 of the body 212 until the support base 230 reaches its second position, as shown in FIGS. 10A and 10B. At this point, the test strip 120 is pressed against the read-head 228, and a substantial portion of the read-head 228 is disposed outside the open cavity 211.

The support base 230 may be locked in its second position by any suitable locking mechanism. For example, a spring-loaded latch may be attached to the cover 310 and a catch may be attached to the body 212 near its first end 214. The latch may be configured to hook onto the catch and maintain the support base 230 (through the cover 310) in its second position.

A fluid sample, such as blood, may then be deposited on the reaction area 130 of the test strip 120 to determine the concentration of an analyte in that fluid sample. After testing the fluid sample, the test strip 120 can be removed from the slots 302 and 304 before moving the cover 110 back to its closed position. Alternatively, the cover 110 may be moved to its closed position with the test strip 120 inside the meter 10. In this case, the test strip 120 may be disposed of at a later time.

Some embodiments of the present disclosure are further described in the paragraphs below.

Alternative Embodiment A

A system for determining the concentration of an analyte in a fluid sample, comprising:

a test strip having first and second ends, a first end portion adjacent to the first end, a second end portion adjacent the second end, and a central portion between the first and second end portions and remote from the first and second ends, the central portion of the test strip including a reagent adapted to react with an analyte in a fluid sample and to produce a reaction indicative of the concentration of the analyte in the fluid sample, the first and second ends having first and second elongated slots, respectively;

a meter having a body having first and second ends and defining a longitudinal axis extending between the first and second ends, the meter comprising:

a first movable portion movably coupled to the body and movable along the longitudinal axis between a first position and second position;

a second movable portion movably coupled to the first movable portion and at least partially disposed between the first movable portion and the body;

a read-head adapted to analyze the reaction between the analyte and the reagent, the read-head having a tapered read portion protruding from the second end of the body;

a first spring connected to the first movable portion and biasing the first movable portion to the second position;

a second spring connected to the second movable portion and biasing the second movable portion to the second position; and a cover pivotably coupled to the first movable portion and movable between a closed position.

Alternative Embodiment B

The system of embodiment A, wherein when the first movable portion is in the first position, the first movable portion is adjacent the first end of the body.

Alternative Embodiment C

The system of embodiment B, wherein when the first movable portion in the second position, the first movable portion is remote from the second end of the body.

Alternative Embodiment D

The system of embodiment A, wherein the second movable portion is movable along the longitudinal axis between a first position and a second position.

Alternative Embodiment E

The system of embodiment D, wherein when the second movable portion is in the first position, the first movable portion is adjacent the first end of the body

Alternative Embodiment F

The system of embodiment E, wherein when the second movable portion is in the second position, the first movable portion is remote from the second end of the body.

Alternative Embodiment G

The system of embodiment F, wherein the second movable portion has first and second arms oriented substantially parallel to each other and spaced apart from one another so as to define a space therebetween.

Alternative Embodiment H

The system of embodiment G, wherein the first and the second arms having first and second slots, respectively, each of the first and second slots being dimensioned to receive at least a portion of the test strip.

Alternative Embodiment I

The system of embodiment G, wherein the tapered read portion is at least partially aligned with the space defined between the first and second arms of the second movable portion.

Alternative Embodiment J

The system of embodiment A, wherein the first spring is partially disposed within the body and has a first spring constant.

Alternative Embodiment K

The system of embodiment J, wherein the second spring is partially disposed within the body and has a second spring constant, the first spring constant being less than the first spring constant.

Alternative Embodiment L

The system of embodiment A, wherein the cover has a covering portion and connection portion, the covering portion being oriented substantially perpendicular to the connection portion.

Alternative Embodiment M

The system of embodiment A, wherein when the cover is in a closed position, the cover is positioned over the tapered head of the read-head.

Alternative Embodiment N

The system of embodiment M, wherein when the cover is in an open position, the cover is not positioned over the tapered head of the read-head.

Alternative Embodiment O

The system of embodiment A, further comprising a hinge pivotably connecting the connection portion of the cover to the body.

Alternative Embodiment P

A system for determining the concentration of an analyte in a fluid sample, comprising:

a test strip including a reagent adapted to react with an analyte in a fluid sample and to produce a reaction indicative of the concentration of the analyte in the fluid sample; and a meter including a body having first and second ends, the body defining a longitudinal axis extending between the first and second ends, the meter further comprising:

a read-head movably coupled to the body and adapted to analyze the reaction between the analyte and the reagent, the read-head being movable along the longitudinal axis of the body between a first position, in which the read-head is substantially disposed within the body, and a second position in which the read-head is substantially disposed outside the body.

It will be appreciated that that the various features set forth herein can be combined in different ways than presented in the present description. It will also be appreciated that the features described in connection with individual embodiments may be shared with other of the described embodiments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A meter for determining a concentration of an analyte in a fluid sample provided on a test strip, the meter comprising:
   a body having first and second ends, the body defining a longitudinal axis extending between the first and second ends;
   a read-head coupled to the body and adapted to analyze the analyte on the test strip; and
   a test strip holder coupled to the body, the test strip holder having first and second arms,
   wherein the test strip holder is movable relative to the body along the longitudinal axis of the body between a first position, in which the first and second arms of the test strip holder overlie the read-head, and a second position, in which the read-head extends beyond the first and second arms of the test strip holder.

2. The meter of claim 1, wherein the read-head is tapered.

3. The meter of claim 2, wherein the read-head is frustoconical in shape.

4. The meter of claim 1, wherein the first and second arms are oriented substantially parallel to each other and spaced apart from one another so as to define a space therebetween, and
   wherein the read-head includes a tapered portion, the tapered portion being at least partially aligned with the space defined between the first and second arms.

5. The meter of claim 1, wherein in the first position, the read-head is substantially disposed within the body, and in the second position, the read-head is substantially disposed outside the body.

6. The meter of claim 1, wherein the test strip holder in the first position is remote from the second end of the body, and in the second position is adjacent the second end of the body.

7. The meter of claim 1, further comprising:
   a handling mechanism, the handling mechanism comprising a first movable member and the test strip holder;
   a first spring biasing the first movable member remote from the second end, the first spring having a first spring constant; and
   a second spring attached to one of the first or second arms of the test strip holder and to the body, the second spring having a second spring constant,
   wherein the first spring constant is less than the second spring constant.

8. The meter of claim 1, further comprising a hinged cover having a closed position over the test strip holder and having an open position not over the test strip holder.

9. The meter of claim 1, wherein the read-head comprises an optical read-head configured to illuminate a reagent pad on the test strip and obtain measurement of nonspecular reflected light.

10. The meter of claim 1, wherein the meter further comprises:
    a movable guide portion movably coupled to the body and movable along the longitudinal axis between first and second guide positions, wherein when the movable guide portion is in the first guide position, the movable guide portion is remote from the second end of the body, and when the movable guide portion is in the second position, the movable guide portion is adjacent the second end of the body,
    wherein the test strip holder is movably coupled to the movable guide portion and at least partially disposed between the movable guide portion and the body.

* * * * *